(12) United States Patent
Horton et al.

(10) Patent No.: US 8,361,804 B2
(45) Date of Patent: Jan. 29, 2013

(54) METHOD AND COMPOSITION FOR DETERMINING HARDNESS IN WELLBORE FLUID FILTRATE

(75) Inventors: Robert L. Horton, Sugar Land, TX (US); Bethicia B. Prasek, The Woodlands, TX (US)

(73) Assignee: M-I L.L.C., Houston, TX (US)

( * ) Notice: Subject to any disclaimer, the term of this patent is extended or adjusted under 35 U.S.C. 154(b) by 0 days.

(21) Appl. No.: 13/120,541

(22) PCT Filed: Sep. 21, 2009

(86) PCT No.: PCT/US2009/057706
§ 371 (c)(1),
(2), (4) Date: Mar. 23, 2011

(87) PCT Pub. No.: WO2010/036620
PCT Pub. Date: Apr. 1, 2010

(65) Prior Publication Data
US 2011/0177608 A1   Jul. 21, 2011

Related U.S. Application Data

(60) Provisional application No. 61/101,040, filed on Sep. 29, 2008.

(51) Int. Cl.
*G01N 31/16* (2006.01)
*G01N 31/22* (2006.01)
*G01N 33/24* (2006.01)

(52) U.S. Cl. ............ 436/163; 436/25; 436/30; 436/164; 436/166; 436/174; 166/250.01; 166/264

(58) Field of Classification Search ................ 436/8, 18, 436/25, 29, 30, 163, 164, 166, 174, 176; 252/408.1; 166/250.01, 264
See application file for complete search history.

(56) References Cited

U.S. PATENT DOCUMENTS

| | | | | |
|---|---|---|---|---|
| 3,159,586 | A * | 12/1964 | Wildenhayn | 436/79 |
| 3,193,355 | A * | 7/1965 | Fuhrmann | 436/72 |
| 3,240,717 | A * | 3/1966 | Johnson | 436/79 |
| 4,868,169 | A * | 9/1989 | O'Laughlin et al. | 514/179 |
| 6,190,611 | B1 * | 2/2001 | Tachino et al. | 422/430 |
| 6,599,748 | B1 * | 7/2003 | Nakajima et al. | 436/39 |
| 7,156,177 | B2 | 1/2007 | Jones et al. | |
| 7,202,090 | B2 * | 4/2007 | Mitsumoto | 436/73 |
| 2008/0176770 | A1 | 7/2008 | Sanders et al. | |

FOREIGN PATENT DOCUMENTS

EP   0975708 A1   2/2000

OTHER PUBLICATIONS

International Search Report and Written Opinion mailed Apr. 30, 2010 for PCT/US2009/057706.

\* cited by examiner

*Primary Examiner* — Maureen Wallenhorst
(74) *Attorney, Agent, or Firm* — Sara K. M. Hinkley; Patrick Traister

(57) ABSTRACT

Disclosed herein is an indicator precursor composition for determining the hardness of a wellbore fluid filtrate, where the composition includes a colorimetric indicator and a buffer, where the buffer may include a salt of a weak acid and a strong base, and where the indicator precursor may be a dry solid. Also disclosed is a method for determining the hardness of a wellbore fluid filtrate.

6 Claims, No Drawings

METHOD AND COMPOSITION FOR DETERMINING HARDNESS IN WELLBORE FLUID FILTRATE

BACKGROUND OF INVENTION

1. Field of the Invention

This invention relates to a method of determining hardness of a wellbore fluid filtrate, and to a composition for determining hardness of a wellbore fluid filtrate.

2. Background Art

Wellbore fluids, commonly referred to as "Mud" provide a number of functions when drilling a wellbore. Wellbore fluids may comprise a slurry of various components in which a solid material is dispersed in a liquid. Filtration of the wellbore fluid thus produces a wellbore fluid filtrate. To insure performance and the integrity of the system, the properties and compositions of wellbore fluids are monitored. One important property of a wellbore fluid is the hardness of the wellbore fluid filtrate, which is a measure of the concentration of divalent cations, typically calcium ions ($Ca^{2+}$), magnesium ions ($Mg^{2+}$), zinc ions ($Zn^{2+}$), and others known to one of minimal skill in the art.

Numerous methods exist to determine the hardness of a wellbore fluid filtrate. One common method includes a titration of an aliquot of the wellbore fluid filtrate using a buffer solution and a colorimetric indicator. Colorimetric indicators are supplied as solutions of the particular indicator dissolved in a buffer, with or without a solvent. Colorimetric indicator solutions useful in determining the hardness of a wellbore fluid filtrate, however, are plagued with short shelf lives and less than ideal toxicity profiles, mainly due to the buffer solutions and/or solvents utilized in the solutions. These issues are exacerbated in oilfield applications, wherein the indicators may be subjected to extreme temperatures, and/or long shelf times due to the remote nature of the enterprise.

Known indicators for determining hardness in a wellbore fluid filtrate include Versenate indicator solution, which comprises calmagite [(1-Naphthalenesulfonic acid, 3-hydroxy-4-[(2-hydroxy-5-methylphenyl)azo] (CAS 3147-14-6)], in a solution of ethylene diamine tetraacetic acid (EDTA), at a pH of greater than 9 provided by a NaOH/NaOAc buffer solution or a $NH_4OH/NH_4Cl$ buffer solution. This solution may further include ethylene glycol and/or propylene glycol as both a solvent and an antifreeze to preserve the solution.

Other indicators comprise Eriochrome Black T indicator (sodium 3-hydroxy-4-[(1-hydroxy-2-naphthyl)azo]-7-nitronaphthalene-1-sulphonate), (CAS 1787-61-7). However, aqueous solutions of Eriochrome Black T are unstable. Accordingly, Eriochrome Black T is provided in a solution commonly referred to in the art as Manver indicator solution. Manver indicator solution typically comprises about 0.1 wt % Eriochrome Black T dissolved in about 90% triethanolamine and about 10% ethanol. The triethanolamine is present to stabilize Eriochrome Black T. Triethanolamine, however may present various health and safety issues.

Accordingly, there is a need for an indicator useful in determining the hardness of a wellbore fluid filtrate. The indicator preferably has a long shelf life, a suitable toxicity profile, and provides both precision and accuracy in determining the hardness of a wellbore fluid filtrate.

SUMMARY OF INVENTION

In a first aspect of the present invention, an indicator precursor composition for determining the hardness of a wellbore fluid filtrate comprises a colorimetric indicator and a buffer comprising a salt of a weak acid and a strong base, wherein the indicator precursor composition is a dry solid.

In another aspect of the present invention, a method to determine the hardness a wellbore fluid filtrate comprises the steps of:
a) providing a sample of wellbore fluid filtrate;
b) combining the sample of wellbore fluid filtrate with a buffer solution to produce a buffered sample, such that the pH of the buffered sample is greater than 7;
c) combining a portion of an indicator precursor composition with the buffered sample to produce an analysis sample; and
d) titrating the analysis sample with a standardized solution of EDTA to the colorimetric end point to determine the hardness of the wellbore fluid filtrate, wherein the indicator precursor composition comprises a colorimetric indicator and an inert filler comprising a salt of a weak acid and a strong base, and wherein the indicator precursor composition is a dry solid.

These and other features, aspects and advantages of the present invention will become better understood with reference to the following drawings, description and claims.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

The new notation numbering scheme for the Periodic Table Groups is used herein as set out in CHEMICAL AND ENGINEERING NEWS, 63(5), 27 (1985).

As used herein, concentrations may be expressed as ppm (parts per million) and/or by a percentage of the material in the total composition. Unless otherwise stated, all percents express a weight percent (wt %), based on the amount of the material or component at issue in the total composition.

For brevity, upper and lower limitations on physical properties and process conditions may be expressed as ranges. However, it is to be understood that such ranges may comprise any combination of those upper and lower limits recited in any combination herein for a particular component, compound, composition, and/or process. While embodiments may be expressed as comprising a particular limitation, it is to be understood for use herein that such compositions may also consist of and/or consist essentially of the same limitations referred to herein as comprising a particular limitation.

Broadly, the present invention generally provides an indicator useful in determining the hardness of a wellbore fluid filtrate. In an embodiment, an indicator precursor composition for determining the hardness of a wellbore fluid filtrate comprises a colorimetric indicator and an inert filler comprising a salt of a weak acid and a strong base, wherein the indicator precursor composition is a dry solid.

The colorimetric indicator of the instant indicator precursor composition preferably comprises a dye which undergoes a reversible color change in the presence of divalent cations. Suitable colorimetric indicators include calmagite [(1-Naphthalenesulfonic acid, 3-hydroxy-4-[(2-hydroxy-5-methylphenyl)azo] (CAS 3147-14-6)], and Eriochrome Black T indicator (sodium 3-hydroxy-4-[(1-hydroxy-2-naphthyl)azo]-7-nitronaphthalene-1-sulphonate), (CAS 1787-61-7).

The instant indicator precursor composition also comprises an inert salt in combination with the colorimetric indicator. The inert salt is preferably the product of a weak acid and a strong base such that the pH of an aqueous solution of the inert salt has a pH of 7 or above. For purposes herein, a weak acid is defined as an acid that does not completely donate all of its hydrogens when dissolved in water. Weak acids thus have higher pKa compared to strong acids, which release all of their hydrogens when dissolved in water. Weak acids do not ionize in a solution to a significant extent; that is, if the acid was represented by the general formula HA, then in aqueous solution a significant amount of undissociated HA still remains. Weak acids in water dissociate as $$HA_{(aq)} \leftrightarrow H^+_{(aq)} + A^-_{(aq)}.$$

The equilibrium concentrations of reactants and products are related by the Acidity constant expression, (Ka):

$$K_a = \frac{[H^+][A^-]}{[HA]}$$

The greater the value of Ka, the more the formation of H+ is favored, and the lower the pH of the solution. The Ka of weak acids varies between $1.8 \times 10^{-16}$ and 55.5. Acids with a Ka less than $1.8 \times 10^{-16}$ are weaker acids than water. Acids with a Ka of greater than 55.5 are strong acids and almost totally dissociate when dissolved in water.

Examples of suitable weak acids include mineral acids and carboxylic acids having a Ka of between $1.8 \times 10^{-16}$ and 55.5. Preferred weak acids include acetic acid, citric acid, boric acid, phosphoric acid, and hydrofluoric acid, with citric acid being still more preferred.

For purposes herein, a strong base is defined as a basic chemical compound that is able to deprotonate very weak acids in an acid-base reaction. Compounds with a pKa of more than about 13 are called strong bases. Common examples of strong bases are the hydroxides of alkali metals (Group 1 metals). Very strong bases are able to deprotonate very weakly acidic C—H groups in the absence of water. Examples of suitable strong bases include potassium hydroxide (KOH), barium hydroxide ($Ba(OH)_2$), caesium hydroxide (CsOH), sodium hydroxide (NaOH), strontium hydroxide ($Sr(OH)_2$), lithium hydroxide (LiOH), and/or rubidium hydroxide (RbOH), with potassium hydroxide being still more preferred.

Suitable inert fillers of the instant indicator precursor composition include salts comprising one or more carboxylic acids and a hydroxide of a Group 1 metal. Preferably, salts comprising citric acid and potassium hydroxide, with potassium citrate monohydrate being still more preferred.

In a preferred embodiment, the inert filler is not deliquescent, is a stable compound or combination of compounds up to a temperature of about 90° C., and is completely soluble in water at a pH of between 7 and 12.

In an embodiment, the instant indicator precursor composition comprises about 0.01 wt % to about 5 wt % of the colorimetric indicator or combination of colorimetric indicators. Within this range, the instant indicator precursor composition preferably comprises greater than or equal to about 0.1 wt % in some aspects, greater than or equal to about 0.5 wt % in other aspects, and greater than or equal to about 0.9 wt % in yet other aspects.

In an embodiment, the instant indicator precursor composition is in the form of a finely divided solid which is readily soluble in water and/or aqueous solutions having a pH above 6.

In an embodiment, the instant indicator precursor composition is added as a dry powder to the solution being analyzed. In another embodiment, the instant indicator precursor composition is dissolved in an aqueous solution which is subsequently added to the solution being analyzed.

The analysis requires a buffer system of sufficient strength and/or concentration to maintain the test system at an exact pH, but does not interfere with or contribute to the response. Since the present test system depends on binding reversal rather than a pH change, however slight or small, the buffer system must be capable of maintaining the entire mixture of analysis sample to a suitable pH. This pH is dependent upon the color transition range of the colorimetric indicator, and should not have a significant effect on the test sensitivity. Buffer systems found to be suitable include NaOH/NaOAc, $NH_4OH/NH_4OAc$, $NH_4OH/NH_4Cl$, and/or wherein the base component of the buffer is imidazole; tris(hydroxymethyl)aminomethane; 2-amino-2-methyl 1,3-propanediol; bis(2-(hydroxyethyl)imino-tris(hydroxymethyl)methane; and/or, 1,3-bis[tris(hydroxymethyl)-methylamino]propane, and the acid component of the buffer is selected from the group consisting of carboxylic acids, and preferably monocarboxylic acids, such as glycolic, lactic, benzoic, and acetic acids. This list is obviously representative and not intended to be a limitation to the selection of suitable buffers.

In an embodiment, the hardness of a wellbore fluid filtrate is determined using a method comprising the following steps of:
a) providing a sample of wellbore fluid filtrate;
b) combining the sample of wellbore fluid filtrate with a buffer solution to produce a buffered sample, such that the pH of the buffered sample is greater than 7;
c) combining a portion of the indicator precursor composition with the buffered sample to produce an analysis sample; and
d) titrating the analysis sample with a standardized solution of EDTA to the colorimetric end point.

In an alternative embodiment, the indicator precursor composition may first be dissolved in an aqueous solution to produce an indicator solution, and at least a portion of the indicator solution may be combined with the buffered sample to produce the analysis sample.

In an embodiment, the titrant is preferably a standardized solution of EDTA in combination with MgO, or the like.

EXAMPLES

The instant indicator precursor composition for determining the hardness of a wellbore fluid filtrate was determined to provide analytical test results that are indistinguishable from those obtained using the current Manver Indicator Solution;
to offer essentially indefinite shelf-life without the need for any stabilizer;
is less expensive than the current Manver Indicator Solution or any other option; and
has a very good HSE profile.

The HMIS rating of the liquid buffer component comprising ~86% of the current Manver Indicator Solution is 2-1-0-J.

The HMIS rating of the instant indicator precursor composition is 0-0-0-A, i.e., having a considerably better HSE profile.

The above conclusions were reached based on laboratory tests which are detailed below.

10 Samples of the instant indicator precursor composition were prepared by measuring ten aliquots of 60 grams of the instant indicator precursor as follows:

1. weighing 59.406 grams of Potassium Citrate Monohydrate and 0.594 grams of Eriochrome Black T in a large, clean mortar and pestle; then grind together the two components into one 60 gram aliquot. When all of the 60 gram aliquots of the indicator precursor are formulated, blend them together until the mixture is uniform in appearance (a light gray fine powder). Take two small samples of the mixture, 0.5 and 5.0 grams, respectively, and mix them with water as follows:

| Sample Size and pH | | | |
|---|---|---|---|
| Amount of water | Amount of solid indicator | pH Specification | Typical pH |
| 50 ml | ½ grams | 7.0 to 10.0 | 7.96 |
| 50 ml | 5 grams | 7.5 to 10.0 | 8.40 |

Check the pH of the two mixtures, making sure they meet the pH specification noted above. The final specifications are solution clarity and color: For each mixture, use a pipette or disposable dropping pipette to draw up liquid from the bottom of the container into the pipette. Make sure there is no sediment appearing in the pipette (i.e., the solution meets the clarity specification) and the color of the solution is intensely blue-violet. Since the second mixture is ten times as concentrated as the first, the intensity of color should be greater for the second mixture than for the first and approaching opacity except when an intense light is viewed through the pipette, whereupon the intensely blue-violet color will be evident (i.e., the solution meets the color specification).

When storing the indicator precursor, a darkened glass bottle fitted with a plastic-lined, opaque cap (i.e., not paper-lined) is used. The plastic-lined cap for the bottle is recommended to prevent caking. If caking should occur over long storage periods, it is a straightforward matter to simply use a metal spatula to break up and pulverize the material again into powder form. This action should have no material effect on the performance of the indicator.

The instant indicator precursor is dispensed using a level measure of the indicator (~50 mg) or even less than a level measure to prevent an excessively intense color that can reduce the facility to see the titration end-point.

Titrations were preformed according to the following procedure:

Procedure:

1. Add 50 mls of deionized water to a titration dish.
2. Add 20 to 40 drops (1-2 mls) of hardness buffer solution to the dish (NH$_4$OH/NH$_4$OAc, pH 11-12).
3. Add about 10 mg of the instant indicator precursor to the mixture.
4. If a wine-red to a purple color develops, the deionized water used in step 1, contains hardness. If there is a color change, add total hardness titrating solution (40 mg/L, 2EPM EDTA or 400 mg/L 20 EPM EDTA) drop wise while stirring until the water turns to a bright blue color.
5. Using the pipette, add 1 ml of filtrate into the titration dish and stir. A wine red to purple color will again develop if calcium and/or magnesium is present in the filtrate solution.
6. Add total hardness titrating solution, stirring continuously, until the sample again turns a bright blue color.

Calculation:

epm Calcium and Magnesium=mls of Hardness Titrating solution used×2 (If the solution strength is 1 ml=2 epm Hardness)

epm Calcium and Magnesium=mls of Hardness Titrating solution used×20 (If the solution strength is 1 ml=20 epm Hardness)

Usually the magnesium ion content is negligible, so the total Hardness is reported as being all Calcium. Therefore:

mg/L Calcium=epm Total Hardness×20

More or less sample can be used to obtain a titration between 1 and 10 mls, in which case the results obtained above should be divided by the ml of sample used.

epm=equivalent parts per million

The following samples were analyzed and the instant indicator precursor composition for determining the hardness of a wellbore fluid filtrate performed essentially identical to the standard Manver indicator solution.

| Sample ID | Total $Zn^{2+}$, $Ca^{2+}$ & $Mg^{2+}$, as $Ca^{2+}$ | | Total $Ca^{2+}$ & $Mg^{2+}$, as $Ca^{2+}$ | |
|---|---|---|---|---|
| | Comparative Manver | Instant Indicator | Comparative Manver | Instant Indicator |
| (a) 16.2 p ZnBr$_2$/CaBr$_2$ | 12.5% | 12.5% | 6.6% | 6.6% |
| (b) 12.7 p ZnBr$_2$/CaBr$_2$ | 11.9% | 11.9% | — | — |
| (c) 9.7 p ZnBr$_2$/CaBr$_2$ | 6.6% | 6.6% | — | — |

It should be understood, of course, that the foregoing relates to preferred embodiments of the invention and that modifications may be made without departing from the spirit and scope of the invention as set forth in the following claims.

What is claimed:

1. A method to determine the hardness of a wellbore fluid filtrate comprising the steps of:
    a) providing a sample of wellbore fluid filtrate;
    b) combining the sample of wellbore fluid filtrate with a buffer solution to produce a buffered sample, such that the pH of the buffered sample is greater than 7;
    c) combining a portion of an indicator precursor composition with the buffered sample to produce an analysis sample; and
    d) titrating the analysis sample with a standardized solution of EDTA to a colorimetric end point to determine the hardness of the wellbore fluid filtrate, wherein the indicator precursor composition comprises a colorimetric indicator and an inert filler comprising a salt of a weak acid and a strong base, and wherein the indicator precursor composition is a dry solid having a Hazardous Materials Identification System rating of 0-0-0-A.

2. The method of claim 1, wherein the indicator precursor composition is first dissolved in an aqueous solution to produce an indicator solution, and at least a portion of the indicator solution is combined with the buffered sample to produce the analysis sample.

3. The method of claim 1 or 2, wherein the colorimetric indicator comprises Eriochrome T.

4. The method of claim 1 wherein the inert filler comprises potassium citrate monohydrate.

5. The method of claim 1, wherein the colorimetric indicator comprises 0.01 wt % to about 5 wt % of the indicator precursor composition.

6. The method of claim 1, wherein the inert filler comprises:

one or more carboxylic acids; and
a hydroxide of a Group I metal.

* * * * *